United States Patent
Bégin-Drolet et al.

(10) Patent No.: US 9,846,261 B2
(45) Date of Patent: Dec. 19, 2017

(54) METHOD AND APPARATUS FOR DETERMINING AN ICING CONDITION STATUS OF AN ENVIRONMENT

(71) Applicant: UNIVERSITÉ LAVAL, Québec, Québec (CA)

(72) Inventors: André Bégin-Drolet, Quebec (CA); Jean Ruel, Quebec (CA); Jean Lemay, Quebec (CA)

(73) Assignee: UNIVERSITÉ LAVAL, Québec, QC ( * ) Notice: Subject to any disclaimer, the term of this patent is extended or adjusted under 35 U.S.C. 154(b) by 496 days.

(21) Appl. No.: 14/404,471

(22) PCT Filed: May 17, 2013

(86) PCT No.: PCT/CA2013/050380
§ 371 (c)(1),
(2) Date: Nov. 27, 2014

(87) PCT Pub. No.: WO2013/177695
PCT Pub. Date: Dec. 5, 2013

(65) Prior Publication Data
US 2015/0110149 A1    Apr. 23, 2015

Related U.S. Application Data

(60) Provisional application No. 61/653,553, filed on May 31, 2012.

(51) Int. Cl.
*G01K 13/02*    (2006.01)
*G01N 25/00*    (2006.01)
(Continued)

(52) U.S. Cl.
CPC ............... *G01W 1/02* (2013.01); *F03D 80/40* (2016.05); *G01N 25/04* (2013.01); *G01W 1/06* (2013.01); *G08B 19/02* (2013.01); *Y02E 10/72* (2013.01)

(58) Field of Classification Search
CPC ........ G01N 25/20; G01N 25/26; G01N 25/00; G01K 17/06; G01K 13/02; G01K 13/12; G01K 17/00
(Continued)

(56) References Cited

U.S. PATENT DOCUMENTS 4,342,539 A    8/1982    Potter
4,631,959 A    12/1986    Motycka
(Continued)

FOREIGN PATENT DOCUMENTS

CA    1245721         11/1988
CA    2535885 A1      3/2005
(Continued)

OTHER PUBLICATIONS

Bégin-Drolet, André et al., "Commissioning of a new ice-free anemometer: 2011 Field tests at WEICan", Measurement Institute of Measurement and Control, vol. 45, Issue 8, May 2012, London, pp. 2029-2040.
(Continued)

*Primary Examiner* — Gail Kaplan Verbitsky
(74) *Attorney, Agent, or Firm* — Norton Rose Fulbright Canada LLP; Alexandre Daoust

(57) ABSTRACT

The method includes receiving a value of a quantity of heat applied to at least a portion of a structure, said structure having a sensor surface exposed to the environment, receiving a temperature measurement of the sensor surface, receiving a wind speed measurement of the environment, receiving an ambient temperature measurement of the environment, determining a heat transfer projection of the sensor area using at least the wind speed measurement, the ambient temperature measurement, and one of the value of a quantity of heat and a target temperature of the sensor surface; comparing the heat transfer projection to an asso-
(Continued)

ciated heat transfer value, and generating a signal indicating the icing condition status based on the comparison.

20 Claims, 7 Drawing Sheets

(51) Int. Cl.
   *G01W 1/02* (2006.01)
   *G01N 25/04* (2006.01)
   *G01W 1/06* (2006.01)
   *G08B 19/02* (2006.01)
   *F03D 80/40* (2016.01)

(58) Field of Classification Search
   USPC .. 374/29, 30, 100, 16, 28, 7, 138, 141, 208, 374/109, 147, 148, 43; 73/861.5, 73, 73/23.36, 861.2
   See application file for complete search history.

(56) References Cited

U.S. PATENT DOCUMENTS

| | | | |
|---|---|---|---|
| 4,967,056 A | 10/1990 | Iwasa | |
| 6,237,861 B1 | 5/2001 | Northrop et al. | |
| 6,452,542 B1* | 9/2002 | Bachinski | G01C 5/005 342/357.75 |
| 6,612,810 B1 | 9/2003 | Olsen et al. | |
| 6,651,515 B2* | 11/2003 | Bernard | G01K 13/02 374/E13.006 |
| 6,890,152 B1 | 5/2005 | Thisted | |
| 7,086,834 B2 | 8/2006 | LeMieux | |
| 7,104,502 B2* | 9/2006 | Otto | B64D 15/20 244/134 F |
| 7,182,575 B2 | 2/2007 | Grabau | |
| 7,487,673 B2 | 2/2009 | Ormel et al. | |
| 7,637,715 B2 | 12/2009 | Battisti | |
| 7,674,036 B2 | 3/2010 | Severson | |
| 7,708,524 B2 | 5/2010 | Sundermann et al. | |
| 7,802,961 B2 | 9/2010 | Grabau | |
| 7,880,320 B2 | 2/2011 | Cook | |
| 7,922,449 B2 | 4/2011 | Scholte-Wassink | |
| 7,926,763 B2 | 4/2011 | Froman | |
| 8,038,398 B2 | 10/2011 | Nanukuttan et al. | |
| 8,039,980 B2 | 10/2011 | Mizoue et al. | |
| 8,050,887 B2 | 11/2011 | Ahmann | |
| 8,806,934 B2* | 8/2014 | Goedel | G01K 13/028 73/204.22 |
| 2002/0122001 A1* | 9/2002 | Bachinski | G01C 5/005 342/357.75 |
| 2003/0005779 A1* | 1/2003 | Bernard | G01K 13/02 73/861.65 |
| 2004/0041408 A1 | 3/2004 | Casazza | |
| 2005/0218268 A1 | 10/2005 | Otto et al. | |
| 2008/0151963 A1* | 6/2008 | Sandnas | G01K 13/028 374/109 |
| 2009/0110539 A1 | 4/2009 | Uphues | |
| 2009/0142192 A1 | 6/2009 | LeClair et al. | |
| 2009/0154522 A1* | 6/2009 | Kulczyk | G01K 13/028 374/138 |
| 2009/0246019 A1 | 10/2009 | Volanthen et al. | |
| 2010/0004863 A1 | 1/2010 | Ladow et al. | |
| 2010/0034652 A1 | 2/2010 | Battisti | |
| 2010/0119370 A1 | 5/2010 | Myhr | |
| 2010/0149785 A1 | 6/2010 | Dubuc et al. | |
| 2010/0189560 A1 | 7/2010 | Haraguchi | |
| 2010/0260603 A1 | 10/2010 | Dawson et al. | |
| 2010/0329841 A1 | 12/2010 | O'Neil | |
| 2011/0148112 A1 | 6/2011 | Ormel et al. | |
| 2011/0182732 A1 | 7/2011 | Baba | |
| 2011/0280723 A1 | 11/2011 | Libergren | |
| 2011/0282595 A1* | 11/2011 | Severson | G08B 19/02 702/47 |
| 2012/0285261 A1* | 11/2012 | Goedel | G01K 13/028 73/861.42 |
| 2013/0163636 A1* | 6/2013 | Parsons | G01K 13/028 374/158 |
| 2013/0341464 A1* | 12/2013 | Stothers | H05B 1/0236 244/134 F |

FOREIGN PATENT DOCUMENTS

| | | | |
|---|---|---|---|
| CA | 2647682 A1 | 10/2006 | |
| CN | 102374137 B | 7/2013 | |
| DE | 202006015047 U | 12/2006 | |
| DE | 202006015047 U1 | 12/2006 | |
| DE | 102003032387 A1 | 1/2008 | |
| DK | 200970198 A | 11/2010 | |
| EP | 0407641 B1 | 12/1993 | |
| EP | 1422137 A1 | 5/2004 | |
| FR | 2788600 A1 * | 7/2000 | ............. G01N 17/00 |
| GB | 1049109 | 11/1963 | |
| GB | 2293522 A | 3/1996 | |

OTHER PUBLICATIONS

Homola et al., "Ice Sensors for Wind Turbines", Cold Regions Science and Technology, Nov. 2006, vol. 46, Issue 2, Abstract Only.

* cited by examiner

METHOD AND APPARATUS FOR DETERMINING AN ICING CONDITION STATUS OF AN ENVIRONMENT

FIELD

The improvements generally relate to the field of ice mitigation systems such as de-icing and anti-icing systems, and more particularly to intelligent control thereof to reduce energy consumption.

BACKGROUND

Some known ice mitigation systems are switched on or off manually, which requires human intervention. In other cases, when the icing condition status cannot readily be determined by human intervention, ice mitigation systems are left active more than actually required, or even sometimes permanently, which is a cause of energy waste. Energy waste is a concern in itself, and is particularly a concern in situations of limited energy resources, such as where the ice mitigation system is battery powered for instance.

There thus remained room for improvement.

SUMMARY

A system or method to automatically determine an icing condition status of an environment such as described below can be used in automating the control of an ice mitigation system, for instance, or for other purposes.

In accordance with one aspect, there is provided a method for determining an icing condition status of an environment, the method comprising: receiving a value of a quantity of heat applied to at least a portion of a structure, said structure having a sensor surface exposed to the environment, receiving a temperature measurement of the sensor surface, receiving a wind speed measurement of the environment, receiving an ambient temperature measurement of the environment, determining a temperature projection of the sensor area using the value of the quantity of heat applied, the wind speed measurement, and the ambient temperature measurement, comparing the temperature projection to the temperature measurement of the sensor surface, and generating a signal indicating the icing condition status based on the comparison.

In accordance with another aspect, there is provided an apparatus for determining an icing condition status of an environment, the sensor comprising: a structure having a sensor surface exposed to the environment, a heater positioned to apply a quantity of heat to at least a portion of the structure, a temperature sensor positioned to obtain a temperature measurement of the sensor surface, a controller to receive a wind speed measurement of the environment and an ambient temperature measurement of the environment, a function to determine a heat transfer projection of the sensor area using at least the wind speed measurement, the ambient temperature measurement, and one of the value of a quantity of heat and a target temperature of the sensor surface and a function to compare the heat transfer projection to an associated heat transfer value.

In accordance with another aspect, there is provided a method for determining an icing condition status of an environment, the method comprising: receiving a value of a quantity of heat applied to at least a portion of a structure, said structure having a sensor surface exposed to the environment, receiving a temperature measurement of the sensor surface, receiving a wind speed measurement of the environment, receiving an ambient temperature measurement of the environment, determining a heat transfer projection of the sensor area using at least the wind speed measurement, the ambient temperature measurement, and one of the value of a quantity of heat and a target temperature of the sensor surface; comparing the heat transfer projection to an associated heat transfer value, and generating a signal indicating the icing condition status based on the comparison.

As demonstrated below, the temperature projection can be computed based on the laws of thermodynamics and other measured or predictable parameters. The temperature projection can be compared with the corresponding measured temperature and the likelihood of icing can then be evaluated. If used as an input of or as part of a controller in an ice mitigation system for an anemometer or a windmill, for instance, this method can reduce significantly the amount of energy needed. Moreover, if icing is likely to occur, different actions can be taken such generating a signal indicative of the likelihood of icing. Such a signal can be recorded by a data recording device such as a data logger, for instance.

When icing is likely to occur, actions can be triggered such as activating an ice mitigation system, activating a bearing heating system, storing data in a data recording device such as a data logger, transmitting the signal to a remote location, etc. Henceforth, information on weather conditions with potential risk of icing can be provided and used as desired.

Many further features and combinations thereof concerning the present improvements will appear to those skilled in the art following a reading of the instant disclosure.

DESCRIPTION OF THE FIGURES

In the figures.

DETAILED DESCRIPTION

Figure 1:
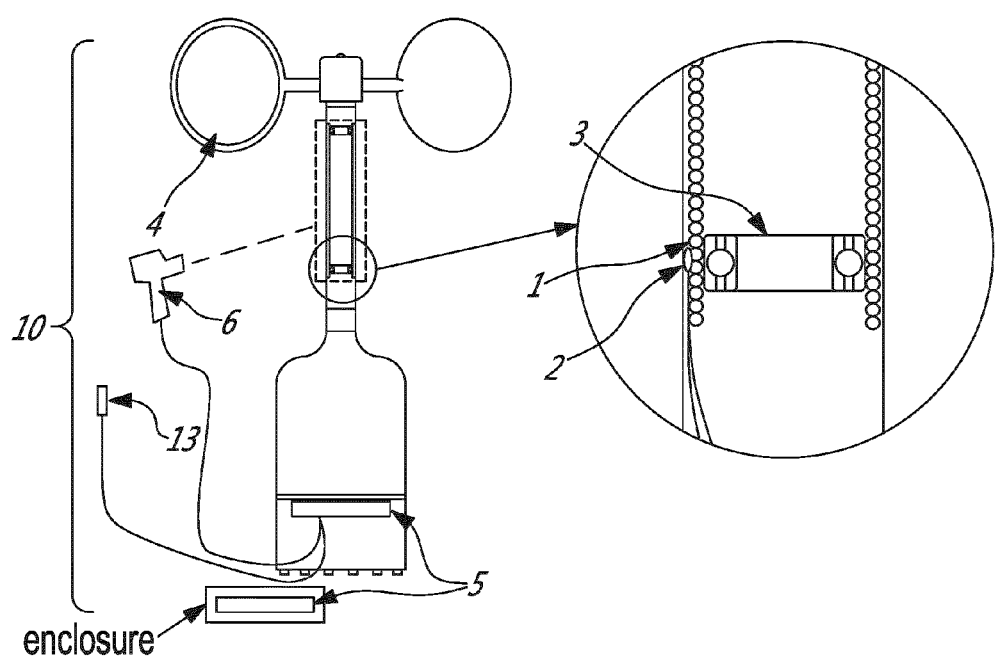
FIG. 1 is a schematic elevation view showing an anemometer including an apparatus for determining an icing condition status of an environment, in accordance with one embodiment.

In an embodiment shown in FIG. 1, an anemometer of the rotary cup type is shown. The anemometer generally has a rotor having a plurality of rotary cups circumferentially interspaced around an axis and rotatably mounted to a base via an elongated shaft. The configuration of the shaft is intended to provide a small disturbance to air flow.

In this embodiment, the shaft forms a structure to which heat is applied and of which an sensor area is exposed to the environment. In this particular embodiment, the shaft is hollow, having a cylindrical wall, and a coiled electrical wire forming a resistor 1 is provided inside the cylindrical wall, placed in contact with an inner face of the cylindrical wall—the outer face being exposed to the environment. Heat is applied to the cylindrical wall by the Joule effect, when a measurable electrical current is circulated through the resistor. The cylindrical wall can be formed of a high electrical conductivity material, such as a metal for instance, to favour uniformity of the temperature of the cylindrical wall. The quantity of heat applied to the cylindrical wall, or heat transfer rate $q_{meas}$, can be determined, by measuring the voltage drop and the current flowing into the resistor and multiplying these two values together, for instance. The heated portion can extend to rotor bearings, for instance, to keep them warm and maintain the predictability of the instrument's calibration curve which is likely to be affected by temperature variations, such as from increased friction which can result from temperature decrease.

The temperature of the sensor surface of the cylindrical wall, which is exposed to the environment can be measured with one or more temperature sensor(s), and will be referred to as $T_{s\_meas}$. In the embodiment illustrated in FIG. 1, thermistors 2 were selected as temperature sensors. If the cylindrical wall is highly conductive, positioning the thermistors against the internal surface of the cylindrical wall, or in apertures provided inside the cylindrical walls for instance, can allow to measure the temperature of the sensor area since the temperature of the outer wall will by very close to the temperature of the inner wall. Alternately, the sensor area temperature $T_{s\_meas}$ can be measured by an external device, such as an infrared sensor 6 for instance. It will be understood that in alternate embodiments, the sensor area can be located on another structure portion, examples of which can include the cups, a portion of the base, or even a portion which does not form part of the anemometer itself as will be detailed below. Further, as will be seen below, more than one sensor area can be used. The ambient temperature of the environment will be referred to as $T_\infty$, and can be measured by any suitable temperature sensor, such as a thermistor 13 for instance. The wind speed of the environment, which will be referred to as $U_{meas}$, can be obtained from the anemometer itself in this embodiment. A controller 5 which can include a microprocessor and can be provided separately from the anemometer or conveniently embedded in the base thereof, for instance, can receive signals representative of $U_{meas}$, $T_{meas}$, $T_\infty$, $q_{meas}$, etc.

The conditions of the environment will affect the surface temperature $T_{s\_meas}$ of the sensor area. For instance, if the ambient temperature $T_\infty$ decreases, while every other parameter remains constant, the surface temperature will decrease as well. In the same way, if the wind speed $U_{meas}$ increases, the surface temperature $T_{s\_meas}$ will decrease since the convection coefficient will increase and more heat will be removed from the heated surface. If the heat transfer rate q is increased, while all other parameters remain constant, the surface temperature $T_{s\_meas}$ will increase. Given necessary obedience to the laws of physics and given apparatus features, a relationship can be established between the surface temperature $T_{s\_meas}$, and the outside conditions, namely the measured wind speed $U_{meas}$, the ambient temperature $T_\infty$ and the measured heat transfer rate $q_{meas}$, which can allow to determine a temperature projection of the sensor area. Environment conditions such as precipitation or icing for instance, can cause the measured temperature of the sensor area $T_{s\_meas}$ to differ from the temperature projection. Henceforth, comparing the temperature projection to the measured temperature of the sensor area, which can be done by the controller for instance, can allow to determine an icing condition status. An associated signal can then be generated, such as by the controller for instance. The signal can be in any suitable form such as frequency-based, voltage-based, and/or current-based, for instance.

In one embodiment, the temperature of the sensor area is controlled in order to maintain it constant independently of external conditions. Henceforth, a target temperature can be set.

The theoretical heat transfer rate required a $q_{theo}$ to keep the surface at a given temperature $T_{s\_meas}$ can be expressed as equation 1.

$$q_{theo}=f(T_\infty, U_{meas}, T_{s\_meas})\qquad\text{eq. 1}$$

If precipitations are occurring, the heat transfer rate theoretically required $q_{theo}$ will be lower than the heat transfer rate actually required because water will contribute to extract more heat from the sensor surface. The control of the heat transfer rate can be done by the controller for instance, to ensure that the surface temperature remains constant at a given value by adjusting the heat transfer rate $q_{meas}$ of the heating element. A difference, which can be referred to as an error, can be obtained by comparing the measured heat transfer rate $q_{meas}$ to the heat transfer rate theoretically required $q_{theo}$ to maintain the surface at a given temperature $T_{s\_meas}$ under given meteorological conditions $U_{meas}$ and $T_\infty$. It will be understood by those skilled in the art that this is equivalent to and indirectly involves comparing a temperature projection to the measured temperature of the sensor area, because the actual measured heat transfer rate $q_{meas}$ is obtained from a measure of the temperature of the sensor area. The reference value (equation 1), the heat transfer rate theoretically required $q_{theo}$, is obtained from a previous calibration and stored in the anemometer's controller 5. If the difference is greater than a given threshold, it can indicate that precipitations are occurring. If the ambient temperature $T_\infty$ is below the freezing point, it is likely that the precipitations would lead to icing, and a signal indicating icing condition status as a presence of icing or a quantitative indication of a likelihood of icing can then be generated.

The generation of the signal can trigger activation of an icing mitigation system, such as heating of the anemometer rotor and bearings, for instance, to prevent biased wind measurements, as well as any suitable alternate action such as transmitting data, or recording data in a data recording device such as a data logger for instance.

In such an embodiment, the theoretical heat transfer rate can be considered to be a heat transfer projection which is then compared with an associated heat transfer value, the actual measured quantity of heat value, to form a basis for the signal generation.

Figure 2:
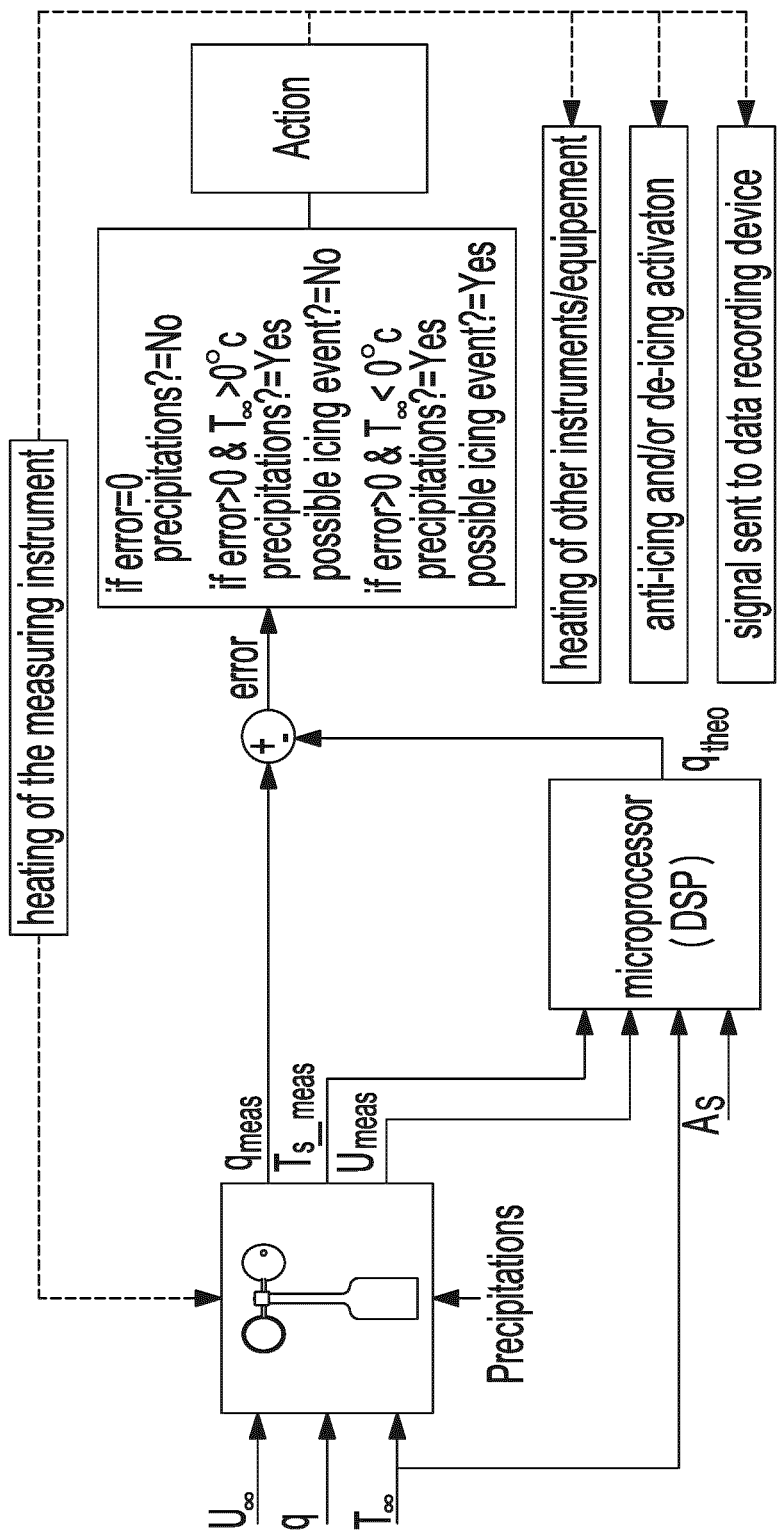
FIG. 2 is a bloc diagram of main components of the apparatus of FIG. 1.

FIG. 2 presents an example control scheme, based on the heat transfer rate theoretically required $q_{theo}$ and the measured heat transfer rate $q_{meas}$, used for the ice detection method to control the activation of the anemometer heating system and/or the heating of other equipment and/or triggering an ice mitigation system such as anti-icing or de-icing mechanisms installed on equipment and/or generating a signal indicative of the presence or likelihood of icing that can be recorded by a data recording device.

In another embodiment, the temperature projection $T_{s\_theo}$ can be theoretically modeled using the expression presented in equation 2.

$$T_{s\_theo}=f(T_\infty, U_{meas}, q_{meas})\qquad\text{eq. 2}$$

In this embodiment, the quantity of heat applied to the sensor area $q_{meas}$ can be constant for instance, rather than being varied to maintain the temperature of the sensor area constant. If precipitations are occurring, the measured surface temperature $T_{s\_meas}$ will be lower than the temperature projection $T_{s\_theo}$ because water will contribute to extract additional heat from the heated zone. The temperature projection for the measured wind velocity $U_{meas}$ and ambient temperature $T_\infty$ is obtained from a previous calibration and stored in the anemometer's controller 5 for instance. The temperature projection can be directly compared to the measured surface temperature to determine a difference, or error, therebetween. If the difference is greater than a given threshold, it can indicate that precipitations are occurring. If the ambient temperature $T_\infty$ is below the freezing point, it is likely that the precipitations would lead to icing, and a signal indicating icing condition status as a presence of icing or a quantitative indication of a likelihood of icing can then be generated.

In such an embodiment, the temperature projection can be considered to be a heat transfer projection which is then compared with an associated heat transfer value, the actual measured temperature of the sensor area, to form a basis for the signal generation.

Figure 3:
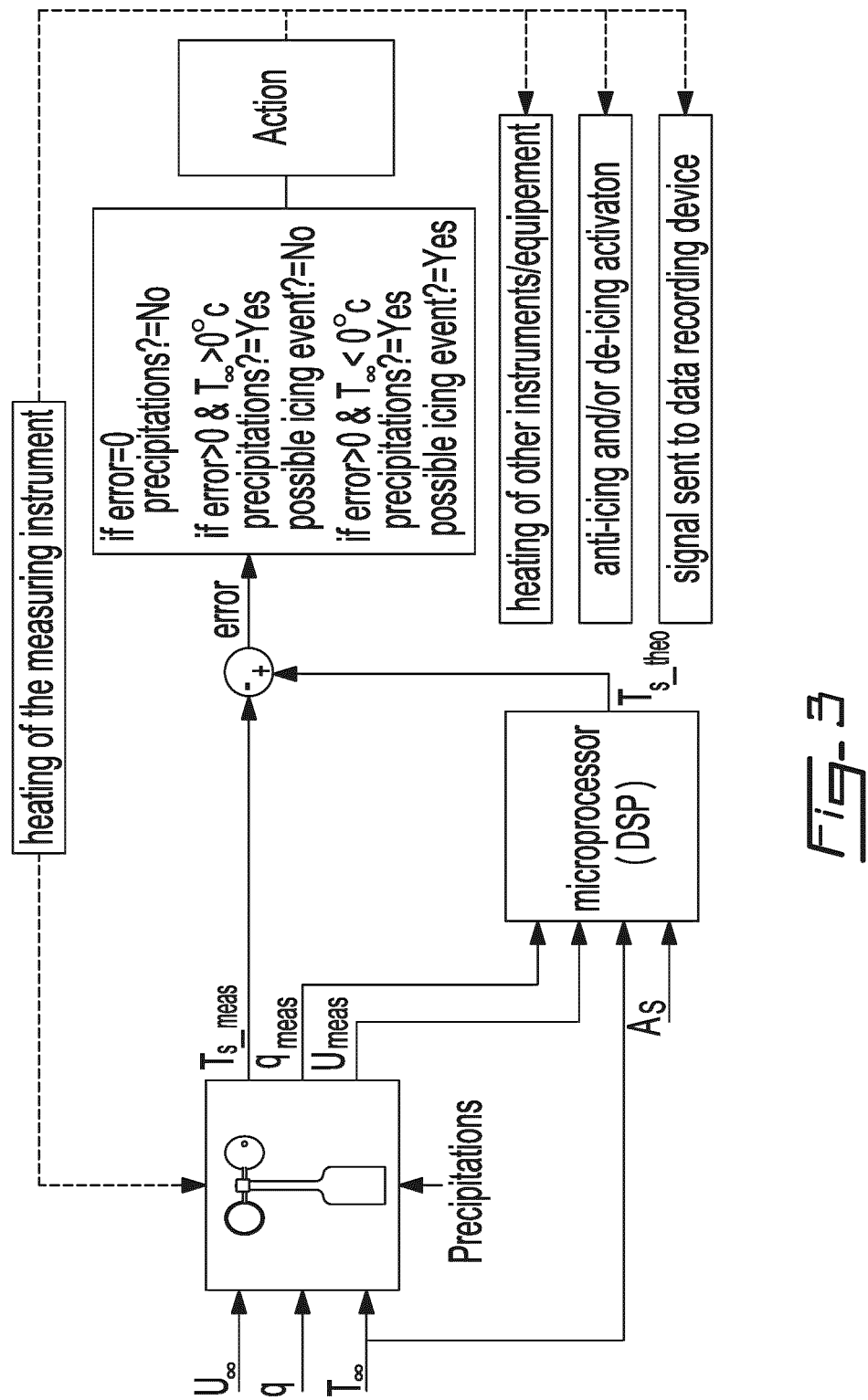
FIG. 3 is a bloc diagram showing an alternative to the apparatus of FIG. 1.

FIG. 3 presents the control scheme, based on the surface temperature measured/modeled, used with the control probe and the thermal model to control the activation of the anemometer heating system and/or an ice mitigation system and/or generating a signal indicative of the likelihood of icing.

The total heat transfer rate from the sensor area can be express by equation 3, the usual convective heat transfer equation also known as Newton's law of cooling, where q is the heat transfer rate, $\bar{h}$ is the average convection coefficient, $A_s$ is the area of the probe, $T_s$ is the surface temperature and $T_\infty$ is the ambient temperature.

$$q = \bar{h} A_s (T_s - T_\infty) \qquad \text{eq. 3}$$

The average convection coefficient can be approximated by a function, for example but not limited to, a second order polynomial equation, such as the one presented in equation 4, where coefficients a, b and c are obtained empirically through calibration. An analytical expression or one obtained through numerical simulations or a look-up table could also be used to describe the average convection coefficient.

$$\bar{h} = a \cdot U_{meas}^2 + b \cdot U_{meas} + c \qquad \text{eq. 4}$$

In one embodiment, the heat transfer rate theoretically needed $q_{theo}$ to keep the surface of a heated volume at a given temperature is obtained using equation 5, which is derived from equations 3 and 4. The heat transfer rate theoretically needed $q_{theo}$ can be calculated according to, but not limited to, equation 5 or an equivalent expression.

$$q_{theo} = (a \cdot U_{meas}^2 + b \cdot U_{meas} + c) A_s (T_{s\_meas} - T_\infty) \qquad \text{eq. 5}$$

The heat transfer rate $q_{meas}$ is measured at any given time and compared with the heat transfer rate theoretically needed $q_{theo}$.

In another embodiment, the temperature projection $T_{s\_theo}$ can be calculated based on equation 6, which is derived from equations 3 and 4, and directly compared to the measured temperature of the sensor area.

$$T_{s\_theo} = \frac{q_{meas}}{(a \cdot U_{meas}^2 + b \cdot U_{meas} + c) A_s} + T_\infty \qquad \text{eq. 6}$$

In still another embodiment, the surface area of the sensor surface to which the heat is being generated is modified so that the exposed surface area $A_s$ can be changed. This embodiment requires to obtain a measurement of the surface area of the sensor area $A_{s\_meas}$ contrary to the embodiments described above where the surface area of the sensor area can be treated as a constant. This can be achieved by changing the surface area of a flexible polymer membrane for instance. The theoretical area needed $A_{s\_theo}$ is calculated according to the surface temperature $T_{s\_meas}$, the measured heat transfer rate from the volume $q_{meas}$, the measured flow velocity $U_{meas}$ and the ambient temperature $T_\infty$, using equation 7, which is derived from equations 3 and 4. The theoretical needed area $A_{s\_theo}$ can be calculated according to, but not limited to, equation 7 or an equivalent expression.

$$A_{s\_theo} = \frac{q_{meas}}{(a \cdot U_{meas}^2 + b \cdot U_{meas} + c)(T_{s\_meas} - T_\infty)} \qquad \text{eq. 7}$$

The surface area of the heated zones $A_{s\_meas}$ is measured at any given time and compared with the theoretical area needed $A_{s\_theo}$. If the theoretical area $A_{s\_theo}$ is larger than that of the measured area $A_{s\_meas}$, it is a sign of precipitations.

In such an embodiment, the surface area required can be considered to be a heat transfer projection which is then compared with an associated heat transfer value—the actual measured surface area of the sensor area, to form a basis for the signal generation.

Figure 4:
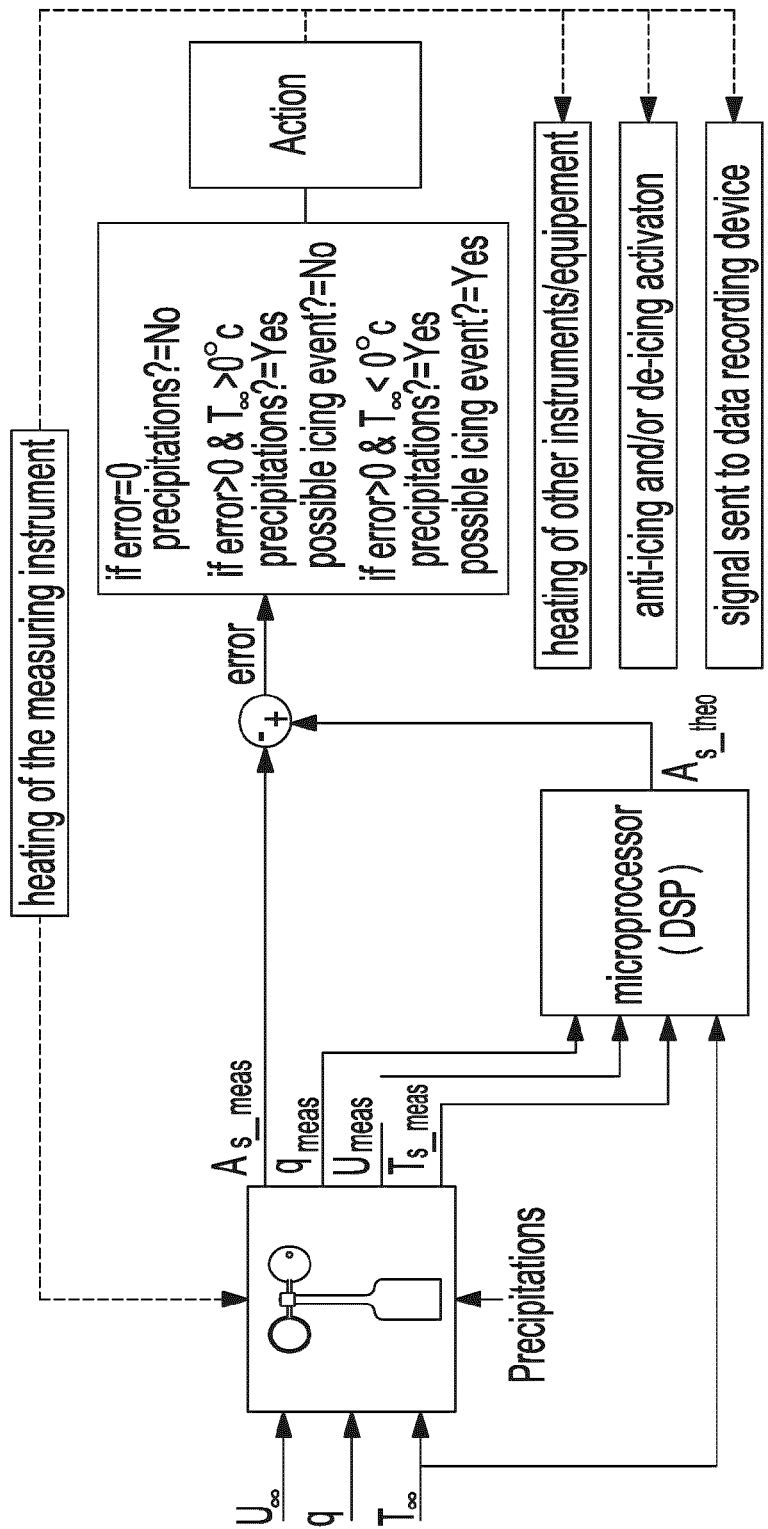
FIG. 4 is a bloc diagram showing another alternative of the apparatus of FIG. 1.

FIG. 4 presents the control scheme, based on the surface area measured/modeled, used to generate a signal indicative of the likelihood of icing which can be used to control the activation of the anemometer heating system and/or an ice mitigation system.

In the embodiment shown in FIG. 1, the anemometer is provided with an ice mitigation system which, in this embodiment, is provided in the form of a heating system for the rotor 4. The heating of the rotor is activated only when a risk of icing is detected while the sensor area can be permanently heated using any suitable strategy which can be based on constant temperature control or a constant power control for instance. Using an intelligent heating strategy for the rotor can allow to minimize the amount of energy consumed by the instrument. In alternate embodiments, the ice mitigation system which can be intelligently controlled based on the signal indicative of icing conditions can be provided on other equipments such as wind turbine components or other ice-sensitive equipment for instance.

Figure 5:
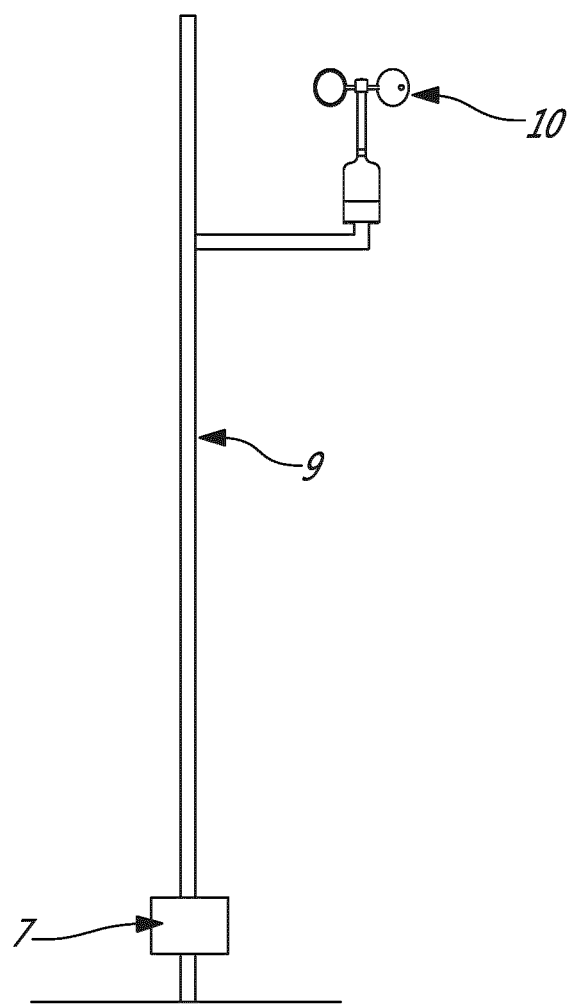
FIG. 5 is an elevation view showing a variant to the apparatus of FIG. 1.

FIG. 5 shows another embodiment where the sensor area is provided externally to the anemometer, but exposed to the same environment. Such a configuration can pose less stringent heating requirements for the bearings of the anemometer, and/or facilitate retro-fitting with an existing anemometer. However, some measuring instruments such as sonic anemometers, do not have moving parts. The functioning of such an alternate embodiment can be similar to that disclosed above in relation with the embodiment shown in FIG. 1.

Figure 6:
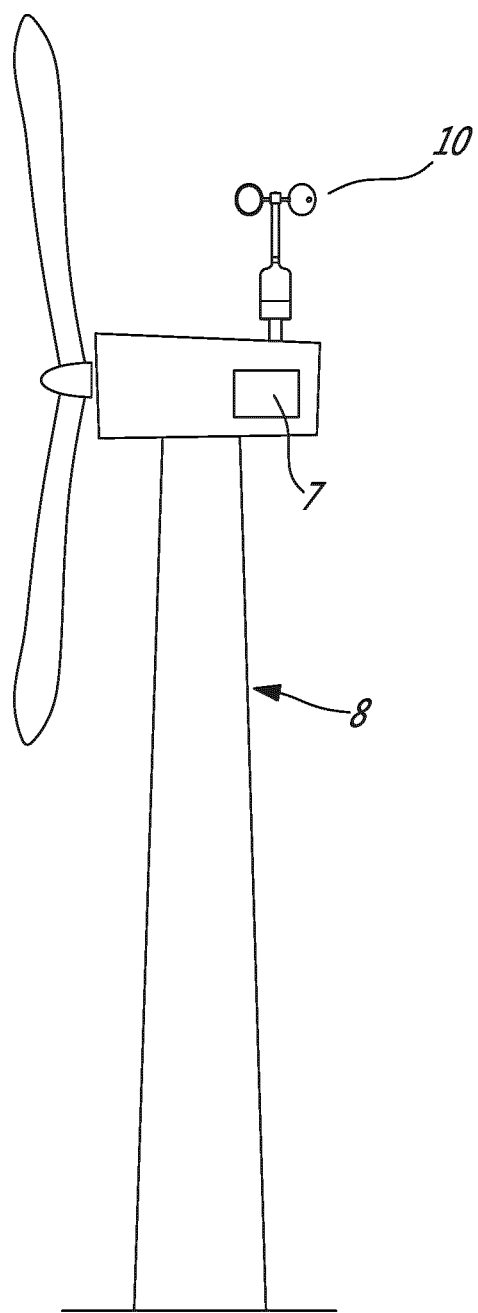
FIG. 6 is an elevation view showing another variant to the apparatus of FIG. 1.

An other alternate embodiment is shown in FIG. 6 in which case the sensor area 7 forms part of a windmill.

Figure 7:
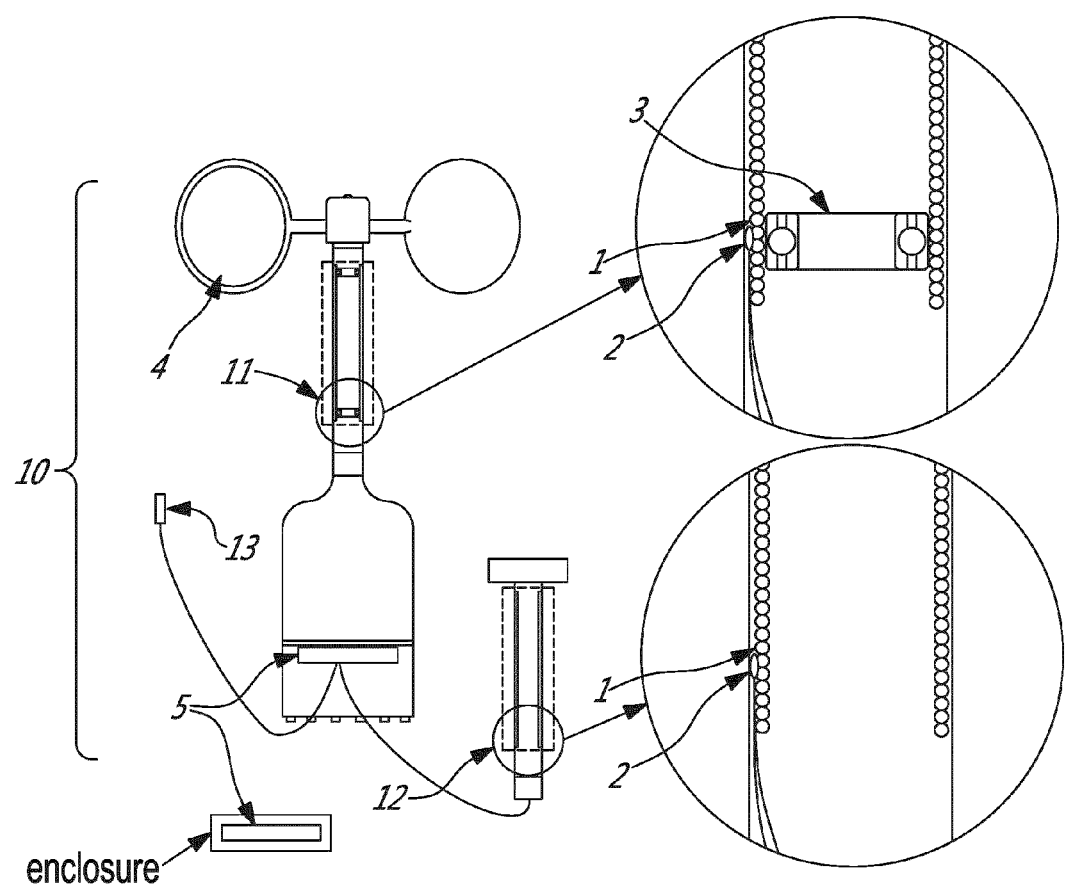
FIG. 7 is an elevation view showing yet another variant to the apparatus of FIG. 1.

A still other alternate embodiment is shown in FIG. 7 which uses two sensor areas. A first sensor area 11 is provided as detailed above with reference to FIG. 1, whereas a second sensor area 12 is provided as part of a cylinder that is positioned adjacent the anemometer. The second sensor area can be kept below the freezing point and the first sensor area can be kept above the freezing point by independently controlling the quantity of heat provided, for instance. The sensor area kept below the freezing point can be used in quantifying the persistence of icing. The persistence of icing, also known as instrumental icing, is an important data since it indicates the total length of an icing event. The sensor area kept at a temperature above the freezing point provides information on the meteorological icing, i.e. the duration of the meteorological event. This data can be useful during wind resource assessment to justify or not the implementation of ice mitigation mechanisms for wind turbines (i.e. anti-icing and/or deicing) at a future given site. Moreover, the zone kept below the freezing point can allow differentiating between a snow event and an icing event. In the case of a snow event, snow will not stick to the surface and will simply make its way around the zone. During an icing event, the ice will grow on the zone affecting its thermal behaviour and icing will be detected. Alternate embodiments can have two sensor area provided in different form, such as both being external to the anemometer or both being part of the anemometer, for instance, or more than two sensor areas.

It will be understood that ice mitigation systems which can be triggered upon an indication of an icing condition status can be de-icing, anti-icing, can be battery powered, grid powered, can be vibratory, heat based, etc. Ice mitigation systems can be used on wind powered devices such as windmills and anemometers, but can also be used on other structures such as on ocean-based platforms, ships, buildings, etc.

As can be seen therefore, the examples described above and illustrated are intended to be exemplary only. The scope is indicated by the appended claims.

What is claimed is:

1. A method for determining an icing condition status of an environment, the method comprising:
   receiving a value of a quantity of heat applied to at least a portion of a structure, said structure having a sensor surface exposed to the environment,
   receiving a temperature measurement of the sensor surface,
   receiving a wind speed measurement of the environment,
   receiving an ambient temperature measurement of the environment,
   determining a heat transfer projection of the sensor area using at least the wind speed measurement, the ambient temperature measurement, and one of the value of a quantity of heat and a target temperature of the sensor surface;
   comparing the heat transfer projection to an associated heat transfer value, and
   generating a signal indicating the icing condition status based on the comparison.

2. The method of claim 1 wherein the heat transfer projection is a quantity of heat projection determined using the target temperature of the sensor surface, and the associated heat transfer value is the value of a quantity of heat applied.

3. The method of claim 2 further comprising varying the value of a quantity of heat based on said comparison.

4. The method of claim 1 wherein the heat transfer projection is a temperature projection determined using the value of the quantity of heat applied, and the associated heat transfer value is the temperature measurement of the sensor surface.

5. The method of claim 1 wherein the icing condition status is one of a presence of icing, an absence of icing, and a quantitative indication of a likelihood of icing.

6. The method of claim 5 further comprising activating an ice mitigation system if the signal indicating the icing condition status indicates one of the presence of icing and the quantitative indication of a likelihood of icing exceeding a given threshold.

7. The method of claim 1 wherein the temperature measurement is done by a temperature sensor located in the structure.

8. The method of claim 1 wherein the determining the heat transfer projection includes obtaining the heat transfer projection from an empirically established table.

9. The method of claim 1 wherein the determining the heat transfer projection includes calculating the heat transfer projection.

10. An apparatus for determining an icing condition status of an environment, the apparatus comprising:
    a structure having a sensor surface exposed to the environment,
    a resistor positioned to apply a quantity of heat to at least a portion of the structure,
    a temperature sensor positioned to obtain a temperature measurement of the sensor surface,
    a controller to receive a wind speed measurement of the environment and an ambient temperature measurement of the environment, a function to determine a heat transfer projection of the sensor area using at least the wind speed measurement, the ambient temperature measurement, and one of the value of the quantity of heat and a target temperature of the sensor surface and a function to compare the heat transfer projection to an associated heat transfer value.

11. The apparatus of claim 10 further comprising an ice mitigation system connected for activation based on the results of said function to compare.

12. The apparatus of claim 10 wherein the temperature sensor is located in the structure.

13. The apparatus of claim 10 wherein the sensor surface is cylindrical.

14. The apparatus of claim 13 wherein the sensor surface is provided in the form of a hollow shaft with the resistor being positioned in the hollow shaft.

15. The apparatus of claim 10, further comprising an anemometer to obtain the wind speed measurement.

16. The apparatus of claim 15 wherein the temperature sensor is a first temperature sensor, further comprising a second temperature sensor to obtain an ambient temperature measurement of the environment.

17. The apparatus of claim 15 wherein the sensor surface and the anemometer are mounted to a windmill.

18. The apparatus of claim 16 wherein the function uses the value of the quantity of heat, the heat transfer projection is a temperature projection of the sensor surface, and the associated heat transfer value is the temperature measurement of the sensor surface.

19. The apparatus of claim 16 wherein the function uses the value of the target temperature of the sensor surface, the heat transfer projection is a quantity of heat projection, and the associated heat transfer value is a quantity of heat measurement.

20. The method of claim 1 further comprising measuring the wind speed of the environment using an anemometer.

* * * * *